US010682198B2

(12) United States Patent
McDowall et al.

(10) Patent No.: US 10,682,198 B2
(45) Date of Patent: *Jun. 16, 2020

(54) METHOD AND SYSTEM FOR FLUORESCENT IMAGING WITH BACKGROUND SURGICAL IMAGE COMPOSED OF SELECTIVE ILLUMINATION SPECTRA

(71) Applicant: Intuitive Surgical Operations, Inc., Sunnyvale, CA (US)

(72) Inventors: Ian E. McDowall, Woodside, CA (US); Christopher J. Hasser, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1070 days.

This patent is subject to a terminal disclaimer.

(21) Appl. No.: 14/937,006

(22) Filed: Nov. 10, 2015

(65) Prior Publication Data
US 2017/0128152 A1    May 11, 2017
US 2018/0116756 A9    May 3, 2018

Related U.S. Application Data

(62) Division of application No. 12/855,864, filed on Aug. 13, 2010, now Pat. No. 9,211,058.

(Continued)

(51) Int. Cl.
*A61B 5/05* (2006.01)
*A61B 90/00* (2016.01)
(Continued)

(52) U.S. Cl.
CPC ............ *A61B 90/37* (2016.02); *A61B 5/0013* (2013.01); *G03B 15/03* (2013.01); *G03B 15/14* (2013.01);
(Continued)

(58) Field of Classification Search
CPC . A61B 90/37; A61B 5/0013; A61B 2090/306;
A61B 2090/304;
(Continued)

(56) References Cited

U.S. PATENT DOCUMENTS 6,148,227 A    11/2000 Wagnieres et al.
6,331,181 B1   12/2001 Tierney et al.
(Continued)

FOREIGN PATENT DOCUMENTS

CN    1627324 A    6/2005
CN    101573068 A   11/2009
(Continued)

OTHER PUBLICATIONS

Bits and Bytes, 12 pages, [Online], Nov. 10, 2014. Retrieved from the internet: URL:http://www.thewonderoflight.com/articles/bits-bytes.
(Continued)

*Primary Examiner* — Jonathan Cwern

(57) ABSTRACT

A surgical site is simultaneously illuminated by less than all the visible color components that make up visible white light, and a fluorescence excitation illumination component by an illuminator in a minimally invasive surgical system. An image capture system acquires an image for each of the visible color components illuminating the surgical site and a fluorescence image, which is excited by the fluorescence excitation component from the illuminator. The minimally invasive surgical system uses the acquired images to generate a background black and white image of the surgical site. The acquired fluorescence image is superimposed on the background black and white image, and is highlighted in a selected color, e.g., green. The background black and white image with the superimposed highlighted fluorescence
(Continued)

image is displayed for a user of the system. The highlighted fluorescence image identifies tissue of clinical interest.

12 Claims, 8 Drawing Sheets

Related U.S. Application Data

(60) Provisional application No. 61/361,260, filed on Jul. 2, 2010.

(51) Int. Cl.

| *G03B 15/03* | (2006.01) |
| *G03B 15/14* | (2006.01) |
| *H04N 5/33* | (2006.01) |
| *A61B 5/00* | (2006.01) |
| *A61B 90/30* | (2016.01) |
| *H04N 13/257* | (2018.01) |
| *H04N 13/239* | (2018.01) |

(52) U.S. Cl.
CPC ........ *H04N 5/332* (2013.01); *A61B 2090/304* (2016.02); *A61B 2090/306* (2016.02); *A61B 2090/373* (2016.02); *A61B 2560/0214* (2013.01); *H04N 13/239* (2018.05); *H04N 13/257* (2018.05)

(58) Field of Classification Search
CPC ...... A61B 2560/0214; A61B 2090/373; H04N 5/332; H04N 13/257; H04N 13/239; G03B 15/14; G03B 15/03
See application file for complete search history.

(56) References Cited

U.S. PATENT DOCUMENTS

| 6,496,719 | B2 | 12/2002 | Hayashi |
| 6,826,424 | B1 | 11/2004 | Zeng et al. |
| 7,330,749 | B1 | 2/2008 | Bhunachet |
| 9,211,058 | B2 | 12/2015 | McDowall et al. |
| 2002/0161282 | A1 | 10/2002 | Fulghum |
| 2003/0135092 | A1 | 7/2003 | Cline et al. |
| 2003/0151735 | A1 | 8/2003 | Blumenfeld et al. |
| 2003/0158470 | A1* | 8/2003 | Wolters .................. A61B 1/043 600/317 |
| 2004/0037454 | A1 | 2/2004 | Ozawa et al. |
| 2004/0245350 | A1 | 12/2004 | Zeng |
| 2006/0013523 | A1 | 1/2006 | Childlers et al. |
| 2007/0046778 | A1 | 3/2007 | Ishihara et al. |
| 2008/0027286 | A1 | 1/2008 | Xie |
| 2008/0065105 | A1 | 3/2008 | Larkin et al. |
| 2009/0192390 | A1* | 7/2009 | Berguer .................. A61B 1/042 600/476 |
| 2009/0236541 | A1 | 9/2009 | Lomnes et al. |
| 2009/0268010 | A1 | 10/2009 | Zhao et al. |
| 2009/0270678 | A1 | 10/2009 | Scott et al. |
| 2009/0312607 | A1 | 12/2009 | Sunagawa et al. |
| 2010/0141748 | A1 | 6/2010 | Yamaguchi |
| 2011/0270057 | A1 | 11/2011 | Pascal |
| 2012/0004557 | A1 | 1/2012 | McDowall et al. |
| 2013/0039562 | A1 | 2/2013 | Watanabe |
| 2016/0089013 | A1 | 3/2016 | McDowall et al. |
| 2017/0128152 | A1 | 5/2017 | McDowall et al. |

FOREIGN PATENT DOCUMENTS

| EP | 2098156 A1 | 9/2009 |
| EP | 2133021 A1 | 12/2009 |
| JP | S63242232 A | 10/1988 |
| JP | H03204089 A | 9/1991 |
| JP | H10500588 A | 1/1998 |
| JP | H10201707 A | 8/1998 |
| JP | 2002095663 A | 4/2002 |
| JP | 2002102145 A | 4/2002 |
| JP | 2002112950 A | 4/2002 |
| JP | 2002112950 A * | 4/2002 |
| JP | 2002299676 A | 10/2002 |
| JP | 2002301009 A | 10/2002 |
| JP | 2004208781 A | 7/2004 |
| JP | 2005111080 A | 4/2005 |
| JP | 2006075189 A | 3/2006 |
| JP | 2006102481 A | 4/2006 |
| JP | 2006134056 A | 5/2006 |
| JP | 2006526767 A | 11/2006 |
| JP | 2007090044 A | 4/2007 |
| JP | 2008539827 A | 11/2008 |
| JP | 2009279168 A | 12/2009 |
| JP | 2010082041 A | 4/2010 |
| JP | 2010082141 A | 4/2010 |
| JP | 2010136769 A | 6/2010 |
| JP | 2010142641 A | 7/2010 |
| WO | WO-2009131840 A1 | 10/2009 |

OTHER PUBLICATIONS

U.S. Appl. No. 12/575,093, filed Oct. 7, 2009.
Office Action dated Apr. 7, 2015 for Japanese Application No. 20130518487 filed Jun. 22, 2011, 11 pages.
PCT/US2011/041479 International Search Report and Written Opinion of the International Searching Authority, dated Sep. 21, 2011, 8 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Jan. 5, 2016 for Japanese Application No. 20130518487 filed Jun. 22, 2011, 11 pages.

* cited by examiner

METHOD AND SYSTEM FOR FLUORESCENT IMAGING WITH BACKGROUND SURGICAL IMAGE COMPOSED OF SELECTIVE ILLUMINATION SPECTRA

RELATED APPLICATION

This application is a divisional application of U.S. patent application Ser. No. 12/855,864 (filed on Aug. 13, 2010), which claims priority to and the benefit of U.S. Provisional Application No. 61/361,260 (filed Jul. 2, 2010, disclosing "METHOD AND SYSTEM FOR FLUORESCENT IMAGING WITH BACKGROUND SURGICAL IMAGE COMPOSED OF SELECTIVE ILLUMINATION SPECTRA"), each of which is incorporated herein by reference in its entirety.

BACKGROUND

Field of Invention

Aspects of this invention are related to endoscopic imaging, and are more particularly related to blending visible and alternate images so as to provide an enhanced real-time video display for a surgeon.

Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery and shorter hospital stay. One key component of the da Vinci® Surgical System is a capability to provide two-channel (i.e., left and right) video capture and display of visible images to provide stereoscopic viewing for the surgeon.

Such electronic stereoscopic imaging systems may output high definition video images to the surgeon, and may allow features such as zoom to provide a "magnified" view that allows the surgeon to identify specific tissue types and characteristics, as well as to work with increased precision. In a typical surgical field, however, certain tissue types are difficult to identify, or tissue of interest may be at least partially obscured by other tissue.

Additional image information of the surgical site may be simultaneously displayed to the surgeon by use of a picture in picture (PIP) display. The additional image information may be useful to the surgeon to improve the surgical outcome. However, the smaller picture in a PIP display may be too small to show a desirable level of detailed information. Moreover with separate image frames, a surgeon mentally fuses the two separate images or imaging modalities together, which can be fatiguing.

SUMMARY

In one aspect, a surgical site is simultaneously illuminated by (i) less than all the visible color illumination components that make up visible white light, sometimes called white light, and (ii) a fluorescence excitation illumination component from an illuminator in a minimally invasive surgical system. An image capture system in the minimally invasive surgical system acquires an image for each of the visible color components illuminating the surgical site, and a fluorescence image excited by the fluorescence excitation illumination component. The minimally invasive surgical system uses the acquired image for each of the visible color illumination components from the illuminator to generate a background black and white image of the surgical site. This background black and white image is referred to as a limited bandwidth image.

The acquired fluorescence image is superimposed on the background black and white image and is highlighted in a selected color, e.g., green. The background black and white image with the superimposed highlighted fluorescence image, referred to herein as an augmented display, is displayed for a user of the system. The highlighted fluorescence image identifies tissue of clinical interest.

The limited bandwidth image with the superimposed highlighted fluorescence image is provided in real time to a surgeon performing a surgical operation using the minimally invasive surgical system. This novel method does not incur the temporal delay necessarily associated with capturing a normal image in one frame and the fluorescence image in another frame and then using the two frames taken at different points in time to generate a single frame that is displayed for the surgeon. Also, the novel method described herein does not result in temporal deficiencies of either latency or combining two frames acquired at different points in time.

The processing for the augmented display does not introduce any latency and does not require storage of a frame for subsequent processing with a later frame. Thus, the memory and processing requirements of the system are reduced with respect to systems that utilize time slicing to superimpose a fluorescence image on a stereoscopic visible image.

Also, the highlighted portion of the image is always synchronized with the background image. In contrast, when a frame including the fluorescence image is stored and then registered to a frame occurring later in time, the location of the highlighted tissue may have changed between the frames and so the highlighted image is displaced from the actual location when displayed. Thus, this novel method is superior for displaying moving tissues such as vasculature where methods containing temporal acquisition mismatches result in displayed motion artifacts which could be disconcerting to the surgeon.

In one example, a plurality of visible color illumination components combines to make white light. An illuminator in the minimally invasive surgical system simultaneously provides at least two illumination components. When one of the illumination components is a fluorescence excitation illumination component, other illumination components provided by the illuminator include less than all the visible color illumination components in the plurality of visible color illumination components.

A camera, in the minimally invasive surgical system, substantially simultaneously captures a first acquired component image, and a second acquired component image that is different from the first acquired component image. A controller is connected to the camera to receive the acquired component images. Herein, substantially simultaneously means simultaneously to the extent that is possible considering temporal differences of elements in the camera in responding to a capture trigger signal issued to the camera.

In one aspect, the controller generates first, second, and third visible color components of a limited bandwidth image. Each of these visible color components includes or is derived from the first acquired component image. The controller adds the second acquired component image to the second visible color component of the limited bandwidth image so that the second visible color component includes both the first acquired component image and the second acquired component image. The limited bandwidth image does not include an acquired visible color component image resulting from at least one of the visible color illumination components of the plurality of visible color illumination components.

The controller generates an image including the limited bandwidth image that is sent to a display connected to the controller. In this aspect, the display receives first, second and third visible color components from the controller. The display shows an image including the limited bandwidth image. A portion of the image including the second acquired component image is highlighted relative to portions of the image not including the second acquired component image.

In one aspect, the other illumination components include a first visible color illumination component. The first acquired component image is an acquired first visible color component image while the second acquired component image is a fluorescence image excited by the fluorescence excitation illumination component.

In another aspect, the other illumination components include the first visible color illumination component and a second visible color illumination component. In this aspect, the camera also captures a third acquired component image. The first acquired component image is an acquired first visible color component image. The second acquired component image is the acquired fluorescence image. The third acquired component image is an acquired second visible color component image. The controller generates the first, second, and third color components of the limited bandwidth image from the acquired first and second visible color component images. In one example, the first visible color component is a blue color component, and the second visible color component is a green color component.

In yet another aspect, the other illumination components are a first visible illumination component and a second fluorescence excitation illumination component. Again, in this aspect, the camera captures a third acquired component image. The first acquired component is the acquired first visible color component image. The second acquired component image is the acquired first fluorescence image. The third acquired component image is an acquired second fluorescence image. The controller adds the third acquired image to the third visible color component of the limited bandwidth image.

In one aspect, the illuminator includes a first visible color illumination component source, a second visible color illumination component source where the second visible color illumination component is different from the first visible color illumination component, and a third visible color illumination component source, where the third visible color illumination component is different from the second visible color illumination component, and different from the first visible color illumination component. The illuminator also includes a fluorescence excitation illumination source.

The minimally invasive surgical system also includes a power level and power supply controller connected to the first, second, and third visible color component illumination sources, and to the fluorescence excitation illumination source. A mode changer is coupled to the power level and power supply controller. The mode changer has a first state and a second state.

When the mode changer has the first state, the power level and power supply controller (a) provides power to the first, second, and third visible color illumination component sources, and not to the fluorescence excitation source, and (b) the first, second, and third visible color illumination component sources have a first level of illumination. When the mode changer has the second state, the power level and power supply controller (a) provides power to the first visible color illumination component source, to at least a portion of the second visible color illumination component source and to the fluorescence excitation source, and not to the third visible color illumination component source, and (b) reduces the levels of illumination of the first visible color illumination component source and the second visible color illumination component source.

In a method of generating an augmented image display in a minimally invasive surgical system, a controller generates a first visible color component of a limited bandwidth image including a first acquired component image. The controller also generates a second visible color component of the limited bandwidth image including the first acquired component image. The controller adds a second acquired component image to the second visible color component. The second acquired component represents fluorescence excited by illumination from a first fluorescence excitation illumination source. The controller generates a third visible color component of the limited bandwidth image including the first acquired component image. The limited bandwidth image does not include an acquired visible color component image resulting from one visible color illumination component in the plurality of visible color illumination components of white light.

The method displays on a display screen, an image including the limited bandwidth image. A portion of the image including the second acquired component image is highlighted relative to portions of the image not including the second acquired component image.

In another aspect of a method of generating an augmented image display in a minimally invasive surgical system, an augmented image correction module is executed on a processor. The execution generates a method that receives, on a first visible color component input of a plurality of visible color component inputs, an acquired first visible color component image. The method also receives, on a second visible color component input of the plurality of visible color component inputs, an acquired fluorescence image.

The method generates, on a first visible color component output, a first signal including the acquired first visible color component image. On a second visible color component output, a second signal including a combination of the acquired first visible color component image and the acquired fluorescence image is generated. Also, on a third visible color component output, a third signal including the acquired first visible color component image is generated. A combination of the first, second and third signals is an image including a limited bandwidth image and the fluorescence image.

This method also receives, on a third visible color component input of the plurality of visible color component inputs, an acquired second visible color component image. In this aspect, the first and third signals include a combination of the acquired first visible color component image and the acquired second visible color component image. The second signal includes the acquired fluorescence image plus the combination of the acquired first visible color component image and the acquired second visible color component image.

In a different aspect, the method receives, on a third visible color component input of the plurality of visible color component inputs, an acquired second fluorescence image. In this aspect, the third signal is a combination of the acquired first visible color component image and the acquired second fluorescence image.

Figure 1:
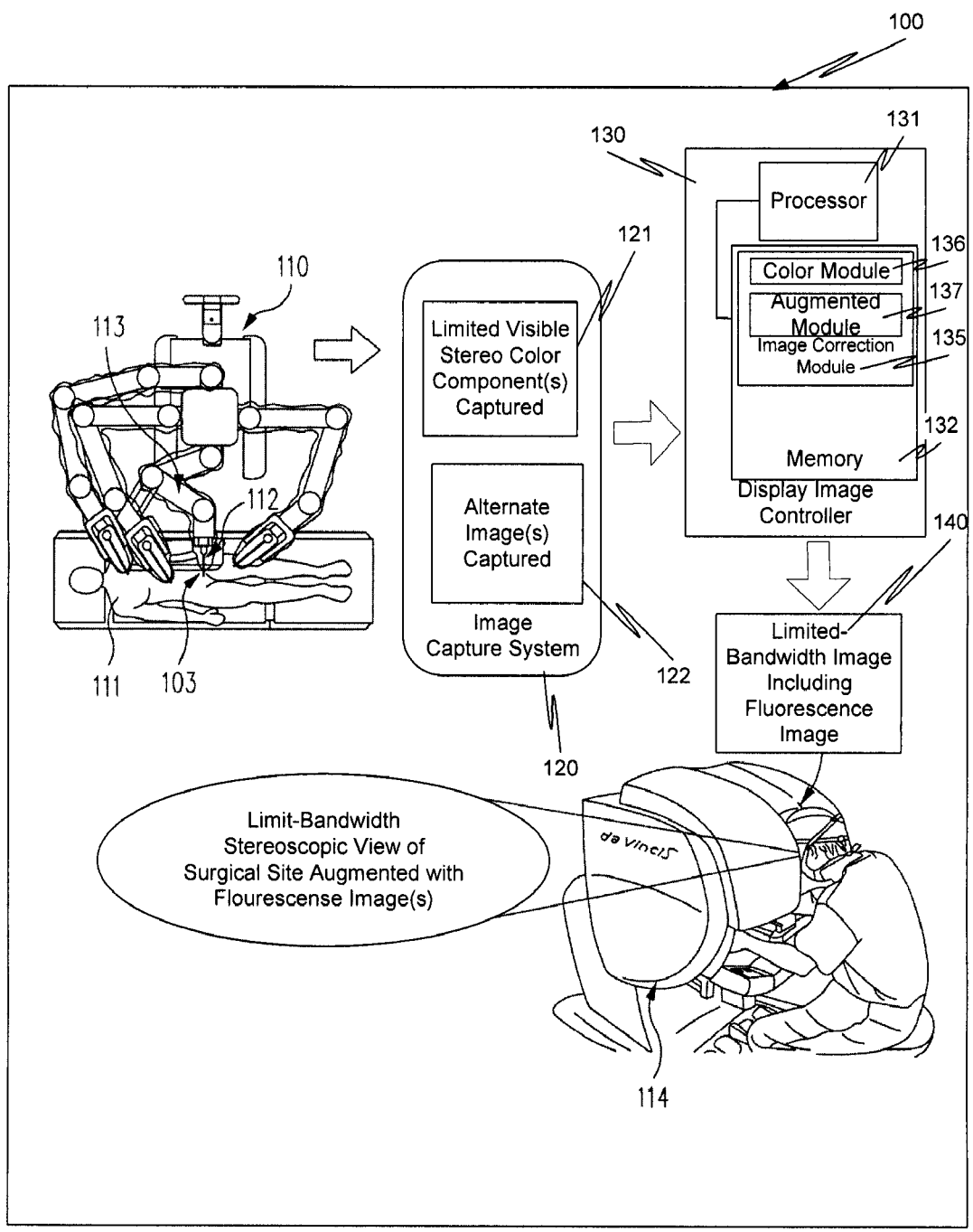
FIG. 1 is a high level diagrammatic view of a minimally invasive teleoperated surgical system including an augmented stereoscopic visualization system.

In the drawings, the first digit of a reference number indicates the figure in which the element with that reference number first appeared.

DETAILED DESCRIPTION

As used herein, electronic stereoscopic imaging includes the use of two imaging channels (i.e., channels for left and right images).

As used herein, a stereoscopic optical path includes two channels in an endoscope for transporting light from tissue (e.g., channels for left and right images). The light transported in each channel represents a different view of the tissue. The light can include one or more images. Without loss of generality or applicability, the aspects described more completely below also could be used in the context of a field sequential stereo acquisition system and/or a field sequential display system.

As used herein, an illumination path includes a path in an endoscope providing illumination to tissue.

As used herein, images captured in the visible electromagnetic radiation spectrum are referred to as acquired visible images.

As used herein, white light is visible white light that is made up of three (or more) visible color components, e.g., a red visible color component, a green visible color component, and a blue visible color component. Thus, white light has a plurality of visible color components. If the visible color components are provided by an illuminator, the visible color components are referred to as visible color illumination components. White light may also refer to a more continuous spectrum in the visible spectrum as one might see from a heated tungsten filament, for example.

As used herein, a black and white image that is generated using an illuminator that provides less than all of a plurality of visible color illuminations components of white light is referred to as a limited bandwidth image.

As used herein, images captured as the result of fluorescence are referred to herein as acquired fluorescence images. There are various fluorescence imaging modalities. Fluorescence may result from the use of, for example, injectable dyes, fluorescent proteins, or fluorescent tagged antibodies. Fluorescence may result from, for example, excitation by laser or other energy source. Fluorescence images can provide vital in vivo patient information that is critical for surgery, such as pathology information (e.g., fluorescing tumors) or anatomic information (e.g., fluorescing tagged tendons).

Aspects of this invention augment the stereoscopic video capturing and viewing capability of a minimally invasive surgical system, e.g., the da Vinci® minimally invasive teleoperated surgical system commercialized by Intuitive Surgical, Inc. of Sunnyvale, Calif., by incorporating both stereoscopic normal visible images, and alternatively stereoscopic limited bandwidth visible images having superimposed thereon fluorescence images. (da Vinci® is a registered trademark of Intuitive Surgical, Inc. of Sunnyvale, Calif.) A stereoscopic limited bandwidth visible image with a superimposed highlighted fluorescence image provides a stereoscopic image of a surgical site with pathology information and/or anatomic information highlighted for the surgeon. The highlighted fluorescence image identifies tissue of clinical interest.

The stereoscopic limited bandwidth image with the superimposed highlighted fluorescence image is provided in real time to a surgeon performing a surgical operation using a minimally invasive teleoperated surgical system. Sequential acquisition approaches (also known as time slicing) incur a delay associated with capturing a stereoscopic image in one frame and the fluorescence image in another frame and then using the two frames taken at different points in time to generate a single frame that is displayed for the surgeon. Hence, the memory and processing requirements of the system described herein are reduced with respect to systems that utilize time slicing to superimpose a fluorescence image on a stereoscopic color visible image.

The stereoscopic limited bandwidth visible image is formed using less than all the plurality of visible color illumination components that make white light and so color information in the limited bandwidth visible image is lost but there is little or no loss in detail. The stereoscopic limited bandwidth visible image is sufficient to identify anatomy, tissue landmarks, and surgical instruments so that this image allows safe manipulation of the surgical instruments. With the limited bandwidth visible image, there is no loss in contrast of the fluorescence image due to interference by a visible color illumination component.

The fluorescence image is overlaid onto the limited bandwidth visible image and color enhanced to provide improved information content regarding the surgical site that reduces the risk of injury to the patient and that improves surgical efficiency. This combination of a stereoscopic limited bandwidth visible image and a highlighted fluorescence image provides benefits including, but not limited to, allowing a surgeon in real-time to identify positive tumor margins for diseased tissue excision and to identify other tissue, e.g., tendons, so as to avoid unnecessarily cutting that tissue.

The combination of the stereoscopic limited bandwidth images and fluorescence images may be continuously displayed to the surgeon. Alternatively, the overlay of the two images may be toggled on and off (e.g., by using a foot pedal or by double-clicking master finger grips on the da Vinci® Surgical System surgeon's console).

FIG. 1 is a high level diagrammatic view of a minimally-invasive teleoperated surgical system 100, for example, the da Vinci® Surgical System, including an augmented stereoscopic visualization system. In this example, a surgeon, using a surgeon's console 114, remotely manipulates an endoscope 112 mounted on a robotic manipulator arm 113.

There are other parts, cables etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), both of which are incorporated herein by reference.

As explained more completely below, an illumination system (not shown), sometimes referred to as an illuminator, is coupled to endoscope 112. The illumination system selectively provides one of (a) white light illumination and (b) less than all the visible color illumination components of white light and at least one fluorescence excitation illumination component. The light from the illumination system is coupled to at least one illumination path in endoscope 112 by a fiber optic bundle (See fiber optic bundle 216 in FIG. 2). The light passes through at least one illumination path in endoscope 112 and illuminates tissue 103 of a patient 111.

Endoscope 112 also includes, in one aspect, two optical channels for passing light from the tissue, e.g., reflected white light or the reflected light from the visible color illumination component(s) and fluorescence. The reflected white light is used to form a normal visible image or images. As explained more completely below, the reflected light from the visible color illumination component(s) is used to form the limited bandwidth visible image.

The white light reflected from tissue 103 is captured as normal acquired visible color stereoscopic images in image capture system 120 when the illumination source is providing white light illumination. However, when the surgeon wants to see an augmented image, the surgeon changes the viewing mode to an augmented viewing mode.

In the augmented viewing mode, at least one of the plurality of visible color illumination components of white light is turned off so that the illumination source provides less than all of the visible color illumination components of white light. For example, if three visible color illumination components of white light are used, at most two visible color illumination components are provided by the illumination source. Thus, in this aspect of the augmented viewing mode, tissue 103 is illuminated with one or two visible color illumination components, e.g., with less than all the plurality of visible color illumination components of white light, and a fluorescence excitation illumination component.

In the augmented viewing mode, acquired left and right visible color component images are captured by element 121 for each visible color component provided by the illuminator and the fluorescence is captured by element 122 as left and right fluorescence images. Image capture system 120 is a conventional image capture system except any filter or filters that would block the fluorescence are removed, and a filter or filters may be used to block capture of any direct light or reflected light from the fluorescence excitation source or sources.

Display image controller 130 receives the acquired information from image capture system 120. When the acquired information is the normal visible color stereoscopic images, display image controller 130 processes the normal acquired visible color stereoscopic images including color correcting the acquired images and sends the color corrected acquired visible color stereoscopic images to the viewer on surgeon's console 114, which displays the images.

Similarly, in the augmented viewing mode, display image controller 130 receives the acquired information from image capture system 120, i.e., an acquired visible stereo color component image for each visible color component provided by the illumination source and the acquired left and right fluorescence images. In the augmented viewing mode, display image controller 130 uses an augmented image correction process in place of the normal color correction process.

The augmented image correction process uses the acquired visible stereo color component(s) images to generate the limited bandwidth image. For example if the illumination source provides two visible color illumination components, i.e., a first visible color illumination component and a second visible color illumination component, the acquired visible color component images are a combination of an acquired first visible color component image and an acquired second visible color component image.

The augmented image correction process in display image controller 130 combines the acquired first and second visible color component images and provides the combination to each of the color component inputs of the display on surgeon's console 114. The display generates the limited bandwidth image. The image is a limited bandwidth image because the image does not include an acquired visible color component image for a third visible color illumination component.

In addition, the augmented image correction process adds the acquired fluorescence image to one of the color component inputs of the display so that one of the color component inputs receives the fluorescence image plus the combination of the acquired first and second visible color component images. The other two color component inputs to the display receive only the combination of the acquired first and second visible color component images. If the fluorescence image is added to the green component, in this example, the surgeon sees a stereoscopic black and white like image of the surgical site with the tissue or other anatomical feature that generated the fluorescence highlighted in green.

Figure 2:
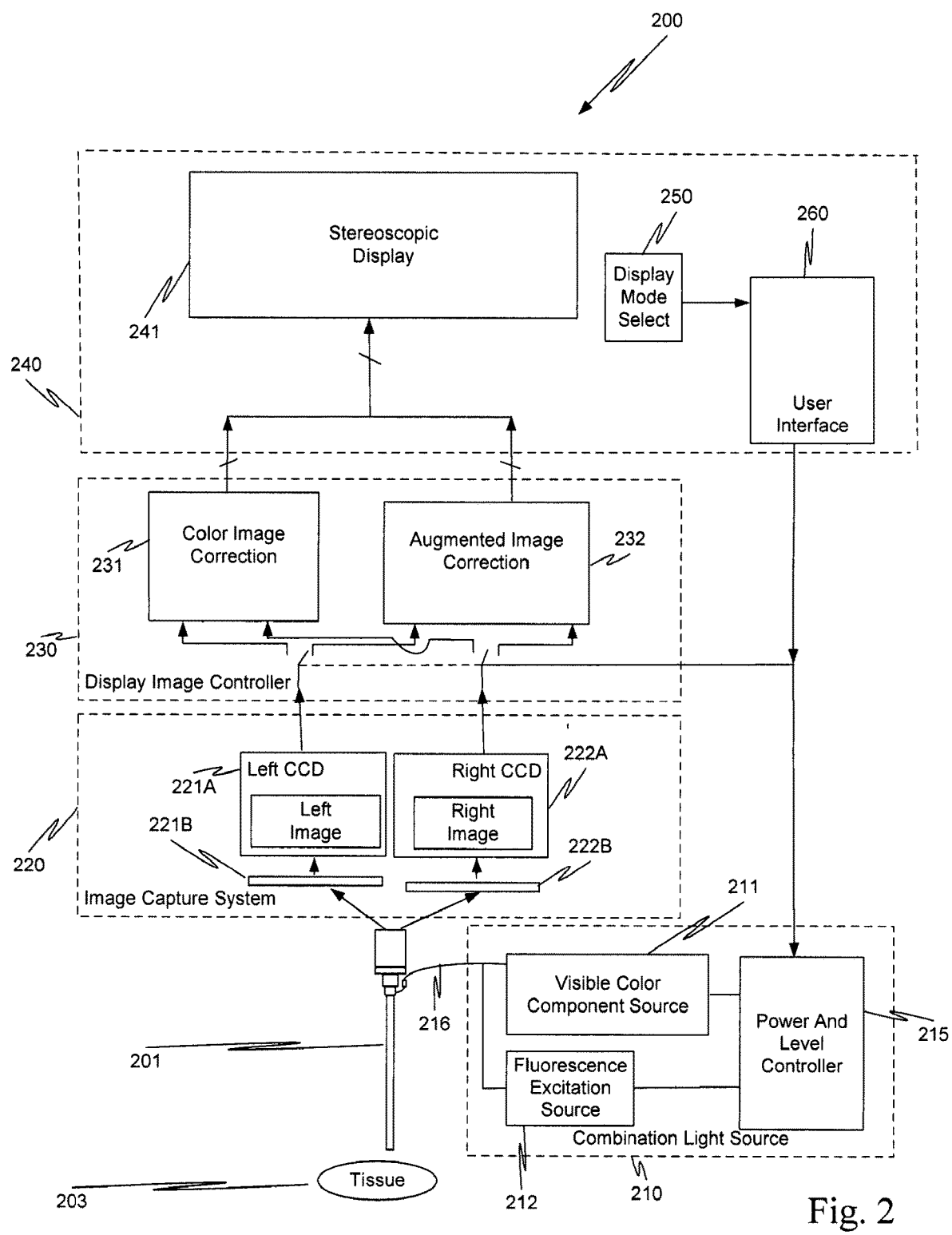
FIG. 2 is a schematic view that illustrates hardware and software (image processing and user interface) aspects of augmented stereoscopic visualization system.
Figure 3:
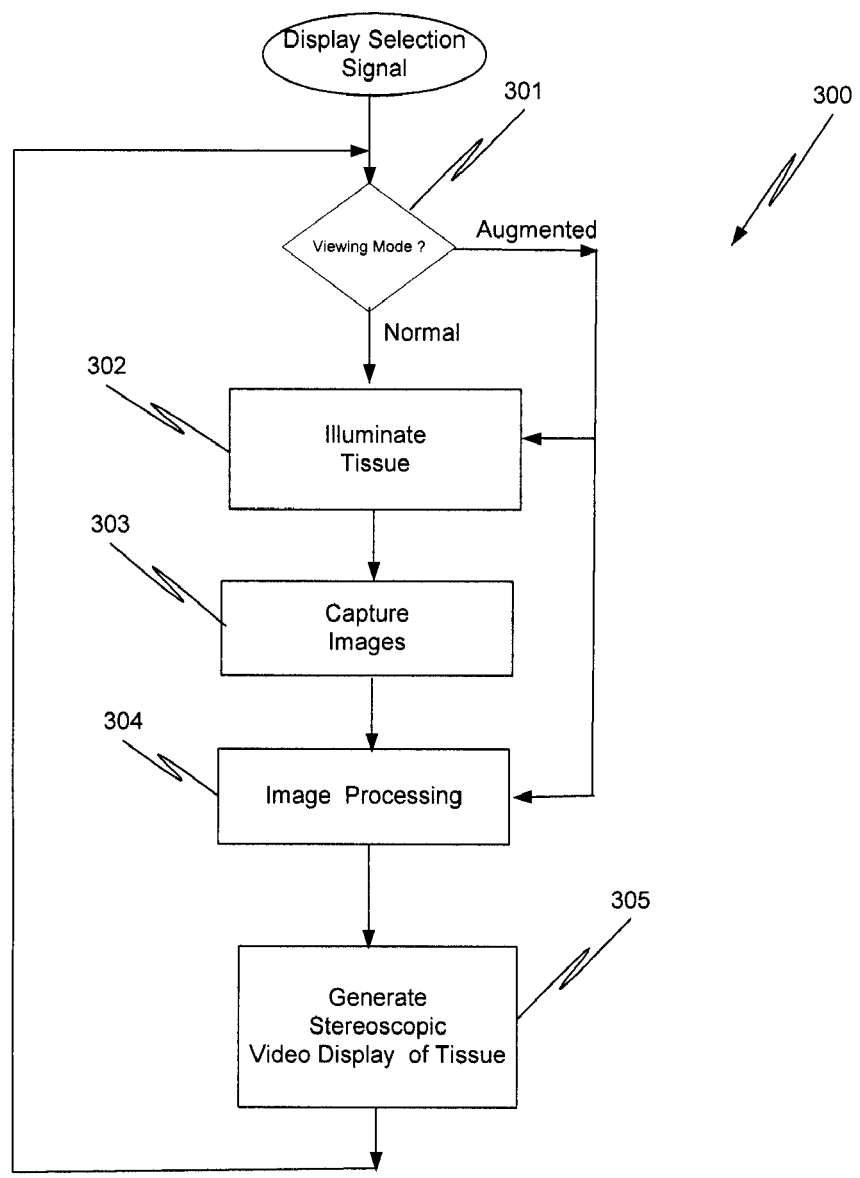
FIG. 3 is process flow diagram of a process performed using, for example, the augmented stereoscopic visualization system of the minimally invasive teleoperate surgical system of FIG. 1.
Figure 4:
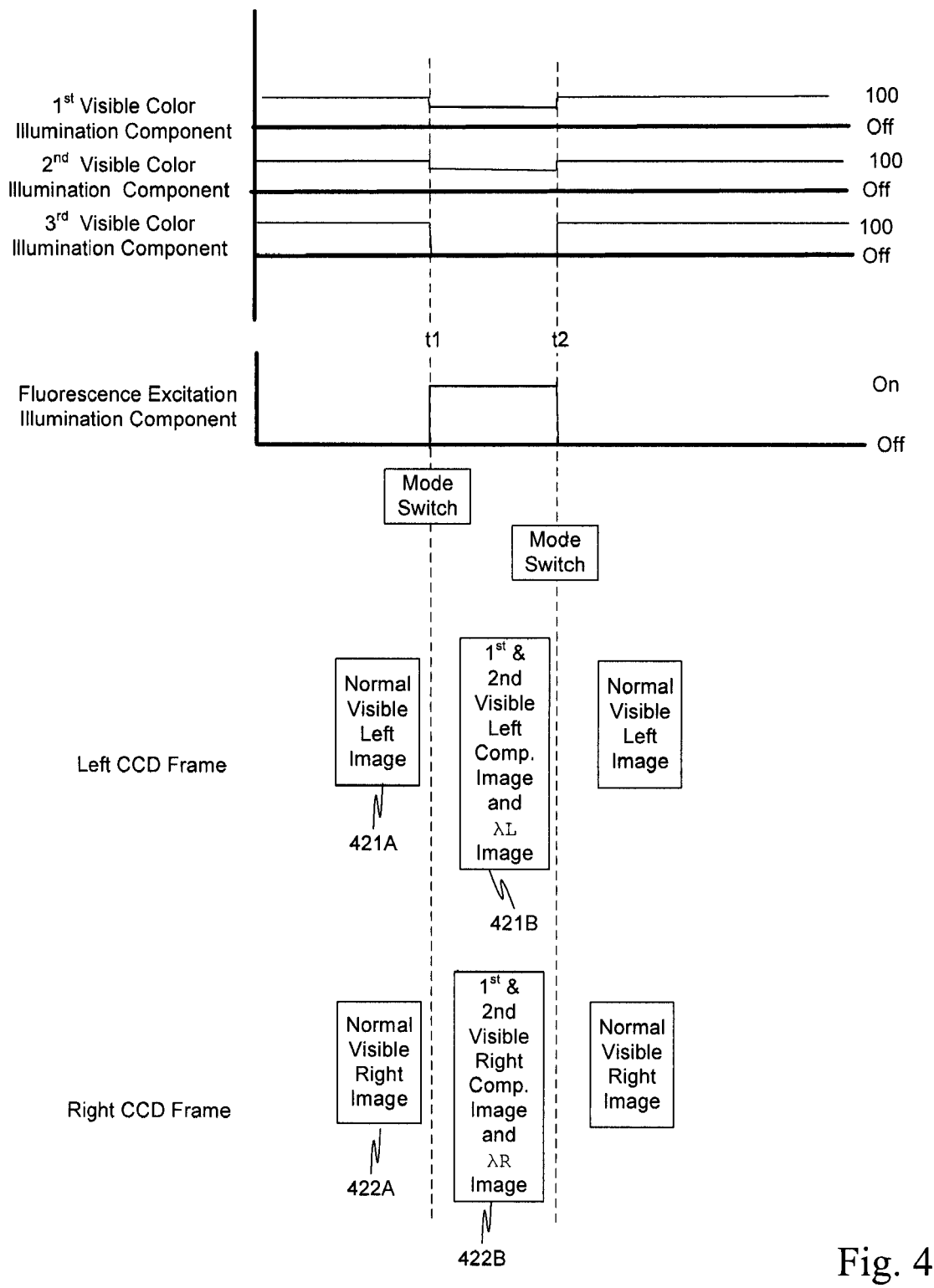
FIG. 4 illustrates one aspect of the timing, synchronization, and capture in the system in FIGS. 2 and 3.

Referring now to FIGS. 2 to 4 together, FIG. 2 is a more detailed illustration of the aspects of one example of minimally invasive surgical system 100 of FIG. 1. FIG. 3 is a process flow diagram for the operation of the system in FIG. 2, while FIG. 4 is a timing diagram for the illumination of tissue and the capture of images in the system of FIG. 2.

In the embodiment of FIG. 2, minimally invasive surgical system 200 includes an illuminator that is combination light source 210. Combination light source 210 includes a visible color component source 211 and a fluorescence excitation source 212. The particular implementation of sources 211 and 212 is not critical so long as combination light source 210 has the capabilities described more completely below.

Combination light source 210 is used in conjunction with at least one illumination path in a stereoscopic endoscope 201 to illuminate tissue 203 in an ILLUMINATE TISSUE process 302 (FIG. 3). In this example, combination light source 210 has two modes of operation: a normal viewing mode and an augmented viewing mode.

In the normal viewing mode, visible color component source 211 provides illumination that illuminates tissue 203 in white light, i.e., all the visible color illumination component sources in source 211 are used. Fluorescence excitation source 212 is not used in the normal viewing mode.

In the augmented viewing mode, visible color component source 211 provides less than all the visible color components needed to illuminate tissue 203 in white light, e.g., one or more of the visible color components of white light are not included in the illumination. In some aspects, for example, it may be possible to use all the visible color illumination components of white light in the augmented viewing mode, but include trivial illumination from one or more of the visible color illumination component sources and augmented viewing mode illumination from the remaining visible color component illumination sources. Trivial illumination means that the illumination provided by the visible color illumination component source is so low that when a trivial illumination image and florescence are acquired together as a common acquired image, the acquired trivial illumination image does not degrade the acquired fluorescence image. Thus, providing trivial illumination for the one or more visible color illumination components is effectively the same as illuminating the tissue with less than all the visible color components of white light.

In one aspect, three visible color components make up white light illumination, i.e., white light includes a first visible color component, a second visible color component, and a third visible color component. Each of the three visible color components is a different visible color component, e.g., a red component, a green component and a blue component. The use of three visible color components to make up white light illumination is illustrative of a plurality of such components and is not intended to be limiting.

In the augmented viewing mode, fluorescence excitation source 212 provides a fluorescence excitation illumination component that excites fluorescence from tissue 203. For example, narrow band light from fluorescence excitation source 212 is used to excite tissue-specific fluorophores so that fluorescence images of specific tissue within tissue 203 are captured.

In the augmented viewing mode, the number of visible color illumination components provided by visible color component source 211 depends on the number of different fluorescence images captured. If one fluorescence image is captured, one or two different visible color illumination components are provided by visible color component source 211 in this example. If two different fluorescence images are captured, one visible color illumination component is provided by visible color component source 211.

In one aspect, visible color component source 211 includes a source for each of the different visible color illumination components in the plurality of visible color illumination components of white light. For a red-green-blue implementation, in one example, the sources are light emitting diodes (LEDs), a red LED, two green LEDs and a blue LED. Table 1 gives the range of output wavelengths for each of the LEDs used in this example.

TABLE 1

| Visible Color Illumination Component | Wavelength |
| --- | --- |
| Red | 670 nanometers (nm) |
| Green 1 | 555 nm |
| Green 2 | 532 nm |
| Blue | 450 nm |

The use of LEDs in visible color component source 211 is illustrative only and is not intended to be limiting. Visible color component source 211 could also be implemented with multiple laser sources instead of LEDs for example. Alternatively, visible color component source 211 could use a Xenon lamp with an elliptic back reflector and a band pass filter coating to create broadband white illumination light for visible images. The use of a Xenon lamp also is illustrative only and is not intended to be limiting. For example, a high pressure mercury arc lamp, other arc lamps, or other broadband light sources may be used. To eliminate one or more visible color illumination components from such a source in the augmented viewing mode, bandpass filters, prisms etc. could be incorporated in combination light source 210.

Also, in the augmented viewing mode if the fluorescence excitation wavelength occurs in the visible spectrum, visible color component source 211 (FIG. 3B) may be used as both the source of the visible color illumination components and the source of the fluorescence excitation illumination component. If the fluorescence excitation wavelength occurs outside the visible spectrum (e.g., in the near infrared (NIR)), a laser module (or other energy source, such as a light-emitting diode or filtered white light) is used as fluorescence excitation source 212.

Thus, in one aspect, fluorescence is triggered by light from a laser module in fluorescence excitation source 212. As an example, antibody agents, which were obtained from Medarex, Inc., were excited using a 525 nm laser.

The particular fluorescence excitation source selected for combination light source 210 depends on the fluorophore or fluorophores used. Excitation and emission maxima of various FDA approved fluorescent dyes used in vivo are presented in Table 2.

TABLE 2

| Fluorescent Dye | Excitation maxima (nm) | Emission maxima (nm) |
| --- | --- | --- |
| Fluorscein | 494 | 521 |
| Indocyanine Green | 810 | 830 |
| Indigo Carmine | 436 in alkaline solution | 528 in alkaline solution |
| Methylene Blue | 664 | 682 |

Table 3 presents examples of common protein fluorophores used in biological systems.

TABLE 3

| Fluorescent proteins/ Fluorophore | Excitation maxima (nm) | Emission maxima (nm) |
| --- | --- | --- |
| GFP | 489 | 508 |
| YFP | 514 | 527 |
| DsRed (RFP) | 558 | 583 |
| FITC | 494** | 518** |
| Texas red | 595** | 615** |
| Cy5 | 650** | 670** |
| Alexa Fluor 568 | 578** | 603** |
| Alexa Fluor 647 | 650** | 668** |
| Hoechst 33258 | 346 | 460 |
| TOPRO-3 | 642 | 661 |

**Approximate excitation and fluorescence emission maxima for conjugates.

Those knowledgeable in the field understand that a fluorophore can be bound to an agent that in turn binds to a particular tissue of the patient. When a particular fluorophore is selected, combination light source 210 includes fluorescence excitation source 212 that provides light with the excitation maxima wavelength for that fluorophore. Thus, given the fluorophore or fluorophores of interest and the number of different fluorophores used, appropriate light sources can be included in combination light source 210.

The above examples in Tables 2 and 3 are illustrative only and are not intended to limit this aspect to the particular examples presented. In view of this disclosure, an alternate imaging characteristic of the tissue can be selected and then an appropriate light source can be selected based upon the fluorescence being utilized.

In either the normal or augmented viewing modes, the light from the light source or light sources is directed into a fiber optic bundle 216. Fiber optic bundle 216 provides the light to an illumination path in stereoscopic endoscope 201 that in turn directs the light to tissue 203.

The video output on stereoscopic display 241 may be toggled between the normal and augmented viewing modes by using, e.g., a foot switch, a double click of the master grips that control the surgical instruments, voice control, and other like switching methods. The toggle for switching between the two viewing modes is represented in FIG. 2 as display mode select 250.

In response to a user input from display mode select 250, a signal is provided to a VIEWING MODE check process 301 (FIG. 3) in a user interface 260 that in turn provides a control signal to an ILLUMINATE TISSUE process 302 when the normal viewing mode is selected. User interface 260, in one aspect, is generated by computer code, which is stored in a memory 132, executing on a processor 131 (FIG. 1).

In one aspect, the normal viewing mode is a default mode. In this aspect, display mode select 250 would not be used until the surgeon wanted to change the viewing mode from the normal viewing mode to the augmented viewing mode, or from the augmented viewing mode to the normal viewing mode.

In the normal viewing mode, ILLUMINATE TISSUE process 302 sends a normal viewing mode operation signal to power and level controller 215 in combination light source 210. Power and level controller 215 is illustrated in combination light source 210 for convenience and is not intended to limit the location of power and level controller 215 to this specific location.

In response to the normal viewing mode operation signal, power and level controller 215 turns off fluorescence excitation source 212, if source 212 is on, and enables visible color component source 211 so that white light is provided to tissue 203. For example, when visible color component source 211 includes three visible color illumination component sources, power is provided to each of the three sources. Those knowledgeable in the field recognize that instead of turning the power on and off to the various sources in 210, controller 215 could maintain the power always on and direct the output from the sources to and away from fiber optic bundle 216 and achieve the same result.

Thus, in the normal viewing mode, ILLUMINATE TISSUE process 302 causes tissue 203 to be illuminated with white light. In the graphs of the illumination in FIG. 4, the horizontal axis is time and the vertical axis represents source output level. The source output level during normal viewing mode operation for each of the three visible color illumination components is defined as 100 percent. Thus, in FIG. 4 for times before time t1, the output level from each of the three visible color illumination components is shown as 100 percent and the output level for the fluorescence excitation illumination component is zero.

The visible light from tissue 203 (FIG. 2) is passed by the stereoscopic optical path in endoscope 201 to image capture system 220. Image capture system 220, in this aspect, includes a conventional stereoscopic camera that includes a left image charge coupled device (CCD) 221A and a right image CCD 222A.

Thus, in CAPTURE IMAGES process 303 (FIG. 3) in the normal viewing mode, left image CCD 221A captures a visible left image 421A (FIG. 4) and right image CCD 222A captures a visible right image 422A. Left image CCD 221A captures red, green, and blue images for visible left image 421A, i.e., the acquired left image is a color image. Similarly, right image CCD 222A captures red, green, and blue images for visible right image 422A.

Left image CCD 221A and right image CCD 222A can be multiple CCDs that each capture a different visible color component; a single CCD with different regions of the CCD that capture a particular visible color component, etc. A three-chip CCD sensor is illustrative only. A single CMOS image sensor with a color filter array or a three-CMOS color image sensor assembly may also be used.

In the normal viewing mode, acquired normal visible left visible image 421A and acquired normal visible right image 422A (FIG. 4) are provided to display image controller 230 (FIG. 2) that performs IMAGE PROCESSING process 304 (FIG. 3). In IMAGE PROCESSING process 304, a COLOR IMAGE CORRECTION process 231 processes both acquired normal visible left visible image 421A and acquired normal visible right image 422A. The color corrected acquired normal visible left visible image and the color correct acquired normal visible right image are sent to stereoscopic display 241 and a stereoscopic color image is displayed in GENERATE A STEREOSCOPIC VIDEO DISPLAY OF TISSUE process 305.

The processing in the normal viewing mode is equivalent to the processing in a conventional minimally-invasive surgical system and so is known to those knowledgeable in the field. Also, processes 301 to 305 are performed repetitively for each frame so that the surgeon sees a real-time video image of tissue 203.

Figure 5A:
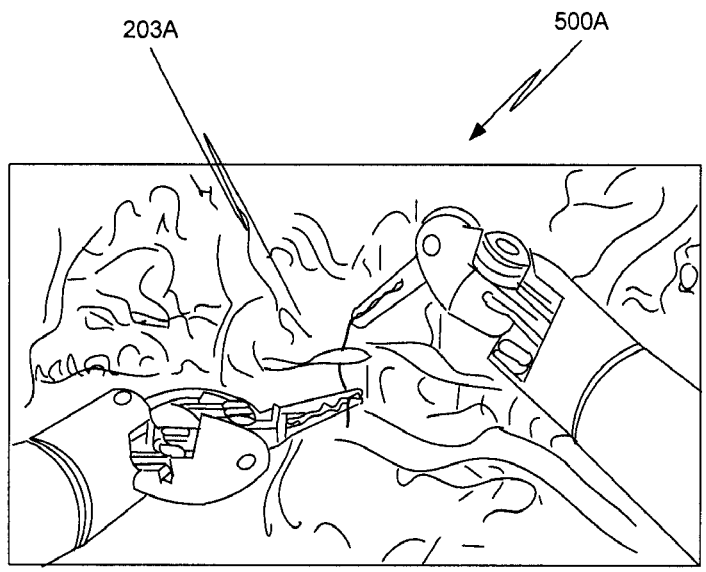
FIG. 5A is a representation of a normal color stereoscopic image obtained using the system of FIG. 2.

During the normal viewing mode, the surgeon is provided with a normal three-dimensional color view 500A of tissue 203A (FIG. 5A). However, the surgeon may wish to see a region or regions of interest in tissue 203A highlighted in the three-dimensional view of tissue 203A. For example, the surgeon may which to see diseased portions of tissue 203A and/or a specific tissue, e.g., a tendon or organ. Thus, at time t1 (FIG. 4), the surgeon uses display mode select 250 to change the viewing mode to the augmented viewing mode.

In response to the user input from display mode select 250, an augmented display selection signal is provided to a VIEWING MODE check process 301 in user interface 260. In response to the augmented display selection signal, check process 301 provides an augmented imaging control signal to ILLUMINATE TISSUE process 302 and to IMAGE PROCESSING process 304.

In response to the augmented display control signal, ILLUMINATE TISSUE process 302 sends an augmented display signal to power and level controller 215 in combination light source 210. In response to the augmented display signal, power and level controller 215 turns on fluorescence excitation source 212 and in this example turns off the third visual color illumination component in visible color component source 211 so that only first and second visual color illumination components and the fluorescence excitation illumination component are supplied to fiber optic bundle 216.

Thus, tissue 203 is illuminated with the first and second visual color illumination components, but not with the third visual color illumination component. Tissue 203 is also illuminated with the fluorescence excitation illumination component 212.

Also, in one embodiment, power and level controller 215 reduces the output level of the first and second visual color illumination components, e.g., reduces the output level to one part in ten. Thus, as shown in FIG. 4, after time t1, the output level of the first and second visual color illumination components is reduced relative to the output level prior to time t1, and the third visual color component illumination output level is zero. Also, the fluorescence excitation illumination component is turned on.

In this example, the fluorescence excited by fluorescence excitation illumination component is captured by the CCD or the part of the CCD for the third visual color component. For example, if the fluorescence is in the near infrared, the third visual color component is the red color component and the first and second visual color components are the blue and green color components.

Alternatively, if the fluorescence were in the range of the green visible color component, the third visible color illumination component would be the green visible color component and would be turned off in source 211, and the first and second visual color components are the red and blue color components. If the fluorescence were in the ultraviolet range, the third visible color illumination component would be the blue color component and would be turned off in source 211, and the first and second visual color components are the red and green color components.

As used herein, "first," "second," and "third" are adjectives used to distinguish between visible color components. Thus, "first," "second," and "third" are not intended to imply any ordering of the visible color components within the visible wavelength spectrum.

In one aspect to assure that there is no incident light on tissue 203 in or near the wavelengths for the visible color illumination component turned off, wavelengths of the adjacent color visible color illumination component(s) that are near or overlap with the wavelengths of the turned-off visible color illumination component are in some way blocked. This assures that the acquired fluorescence image is not degraded by any visible light captured by the CCD that captures the fluorescence image. For example, when visible color component source 211 has the four sources given in Table 1, and the third visible color illumination component is the red visible color component, the green source with wavelengths adjacent to the wavelengths of the red source is also turned off in the augmented viewing mode.

The light from tissue 203 (FIG. 2) are passed by the stereoscopic optical path in endoscope 201 to image capture system 220. In one aspect, filters 221B 222B are used to filter any reflected or direct light from fluorescence excitation source 212 before the images are captured.

In CAPTURE IMAGES process 303 (FIG. 3), in the augmented viewing mode, left image CCD 221A captures acquired left first and second visible color component images and an acquired left fluorescence image 421B (FIG. 4) and right image CCD 222A captures acquired right first and second visible color component images and an acquired right fluorescence image 422B. For example, if the third visible color component is the red visible color component, the blue and green CCDs in left image CCD 221A capture respectively blue and green left visible color component images for the left image. The red CCD in left image CCD 221A captures the left fluorescence image. Similarly, the blue and green CCDs in right image CCD 222A capture respectively blue and green visible color component images for the right image. The red CCD in right image CCD 222A captures the right fluorescence image.

In this example, there is not a third visible color component illumination source, and consequently there is no third visible color component light reflected from tissue 203. This leaves the CCD or portion of the CCD, which normally captures the third visible color component light in the images, available to capture the fluorescence image. Thus, no additional cameras, optic paths in the endoscope, or additional endoscopes are needed to acquire both the visible color component images and the fluorescence image. Herein, when it is stated that a visible color component image in an image is associated with a visible color component illumination source, it means that the visible color component illumination source provides the light that results in that visible color component image in the image.

In the augmented viewing mode, the acquired left first and second visible color component images and the acquired left fluorescence image along with the acquired right first and second visible color component images and the acquired right fluorescence image are provided to display image controller 230 that performs IMAGE PROCESSING process 304. Recall, as described above, IMAGE PROCESSING process 304 has received the augmented display signal. Thus, IMAGE PROCESSING process 304 changes from COLOR IMAGE CORRECTION process 231 to AUGMENTED IMAGE CORRECTION process 232.

Figure 6:
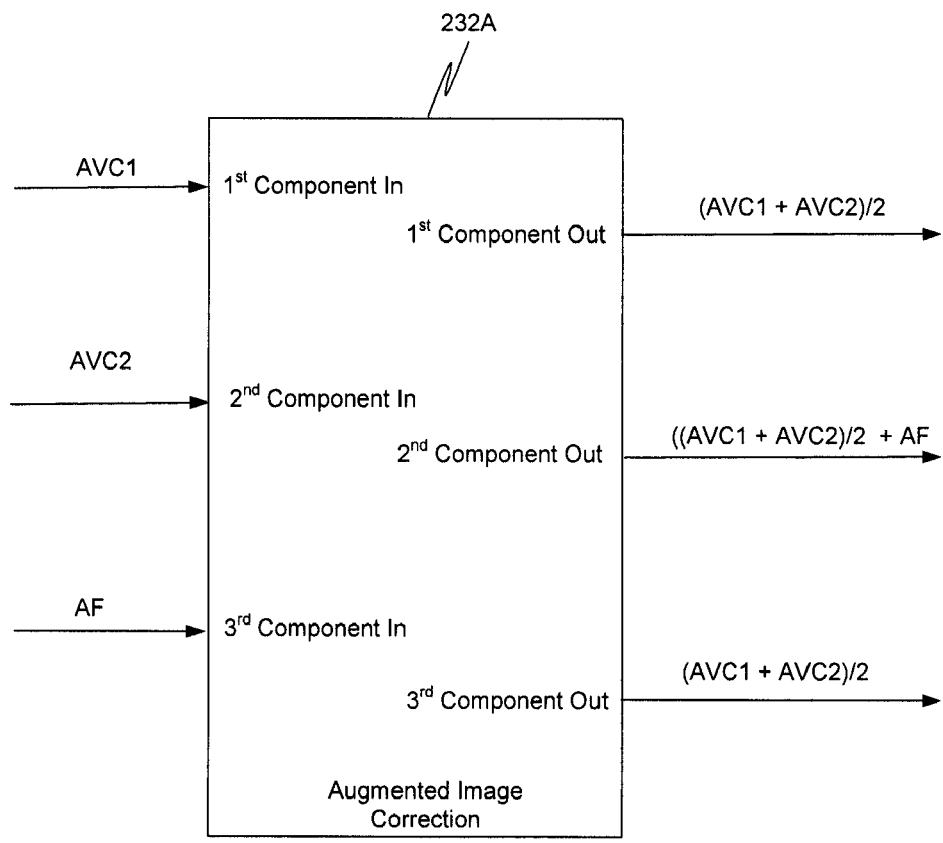
FIG. 6 is a block diagram of one aspect of the augmented image correction process of FIG. 2.

AUGMENTED IMAGE CORRECTION process 232 performs the same process on both the left and right images, and so the left and right designation is not considered in the description. FIG. 6 is a block diagram of the input information to AUGMENTED IMAGE CORRECTION process 232A, and the output information from AUGMENTED IMAGE CORRECTION process 232A for this example.

AUGMENTED IMAGE CORRECTION process 232A receives on a first color component input, acquired first visible color component image AVC1; on second color component input, acquired second visible color component image AVC2; and on a third color component input, acquired fluorescence image AF. AUGMENTED IMAGE CORRECTION process 232A combines acquired first visible color component image AVC1 and acquired second visible color component image AVC2, e.g., forms the average of the two acquired component images for generation of the limited bandwidth visible image. Each color component of the limited bandwidth image is the average of the two acquired visible color component images.

AUGMENTED IMAGE CORRECTION PROCESS 232, in this example, adds acquired fluorescence image AF to second visible color component of the band-width limited image, which is the combination of acquired first visible color component image AVC1 and acquired second visible color component image AVC2. The result of the addition is supplied to the second visible color component output. In this example, the second visible color component output is the output for the visible color component that empirical studies show to be preferred by surgeons, e.g., the green color component.

In this example, the combination of the acquired first visible color component image AVC1 and acquired second visible color component image AVC2 is sent to each of the first and third visible color component outputs. Acquired fluorescence image AF plus the combination of the acquired first visible color component image AVC1 and acquired second visible color component image AVC2 is sent to the second visible color component output. Those knowledgeable in the field understand that the operations described with respect to AUGMENTED IMAGE CORRECTION process 232 are done with respect to a subunit of a frame, e.g., on a pixel by pixel basis and that the "addition" is symbolic and may require undoing and redoing gamma correction for example to achieve a clear image.

The outputs from AUGMENTED IMAGE CORRECTION process 232 are displayed on stereoscopic display 241 (FIG. 2) in GENERATE STEREOSCOPIC VIDEO DISPLAY OF TISSUE process 305 (FIG. 3). In the augmented viewing mode, processes 301 to 305 are performed repetitively so that the surgeon sees a real-time video augmented image of tissue 203.

Figure 5B:
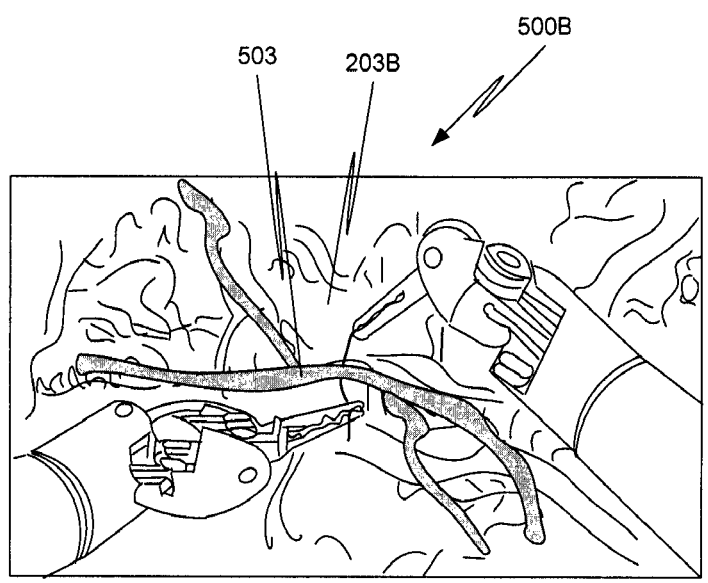
FIG. 5B is a representation of a limited bandwidth stereoscopic image obtained using the system of FIG. 2 with a highlighted superimposed fluorescence image.

During the augmented viewing mode, the surgeon is provided with a three-dimensional limited-bandwidth image of tissue 203 with region of interest 503 (FIG. 5B) highlighted in a particular color. In this example where two visible color component illumination sources were used, the limited-bandwidth image of tissue 203 is a monochrome limited bandwidth image.

While image 203A in FIG. 5A is in full color and image 203B is a limited bandwidth monochromatic image, the level of detail and information in the two images is equivalent, but unit image 203B includes additional highlighted information 503. The switch between the viewing modes for images 203A and 203B is fast and occurs in real time.

The processing for the augmented display does not introduce any latency and does not require storage of a frame for subsequent processing with a later frame. The processing occurs in real time and so the highlighted portion of the three-dimensional image is always synchronized with the limited-bandwidth monochromatic portion of the three-dimensional image. In contrast, when a frame including the fluorescence image is stored and then registered to a frame occurring later in time, the location of the highlighted tissue may have changed and so the highlighted image is displaced from the actual location when displayed.

When the surgeon wants to change the viewing mode back to the normal stereoscopic color image at time t2 (FIG. 4), the surgeon uses display mode select 250 (FIG. 2) to change the viewing mode to the normal viewing mode. In response to the change, fluorescence excitation source 212 is turned off; the third visible color illumination component is turned on; and the first and second visible color illumination components are returned to the full output level. See FIG. 4. The processing is the same as that described above for the normal viewing mode and so is not repeated.

In one aspect, IMAGE PROCESSING process 304 (FIG. 3) is performed by executing an image correction module 135 (FIG. 1), which is stored in memory 132, on a processor 131. In this example, image correction module 135 includes a color module 136 and an augmented module 137. When color module 136 is executed on processor 131, COLOR IMAGE CORRECTION process 231 is performed. When augmented module 137 is executed on processor 131, AUGMENTED IMAGE CORRECTION process 232 is performed. The use of two modules 136, 137 is illustrative. Those knowledge in the art understand that the two modules could be implemented as a single module, for example.

Although, process 304 is described herein as including executing a module on a processor, it is to be appreciated that process 304 with processes 231 and 232 may be implemented in practice by any combination of hardware, software that is executed on a processor, and firmware. Also, the functions, as described herein, may be performed by one unit, or divided up among different components, each of which may be implemented in turn by any combination of hardware, software that is executed on a processor, and firmware. When divided up among different components, the components may be centralized in one location or distributed across system 100 for distributed processing purposes.

The above example is illustrative only and is not intended to be limiting. In the augmented viewing mode, various combinations of fluorescence excitation sources and visible color component illumination sources can be used. For example, a surgeon may want to see both diseased tissue, e.g., a fluorescing tumor, and other specific tissue, e.g., a fluorescing tagged tendon, so as to avoid cutting the tissue. Thus, two different fluorophores are used that require two different fluorescence excitation sources (See FIG. 7) in fluorescence excitation source 212 (FIG. 2).

In response to the augmented display control signal at time t3, ILLUMINATE TISSUE process 302 sends an augmented display signal to power and level controller 215 in combination light source 210. In response to the augmented display signal, power and level controller 215 turns on the two fluorescence excitation illumination components in fluorescence excitation source 212 and in this example turns off the second and third visual color illumination components in visible color component source 211 so that only first visual color illumination component, the first fluorescence excitation illumination component and the second fluorescence excitation illumination component are supplied to fiber optic bundle 216.

Tissue 203 is illuminated with the first visual color illumination component, but not with the second and third visual color illumination components. Tissue 203 is also illuminated with first and second fluorescence excitation illumination components.

Figure 7:
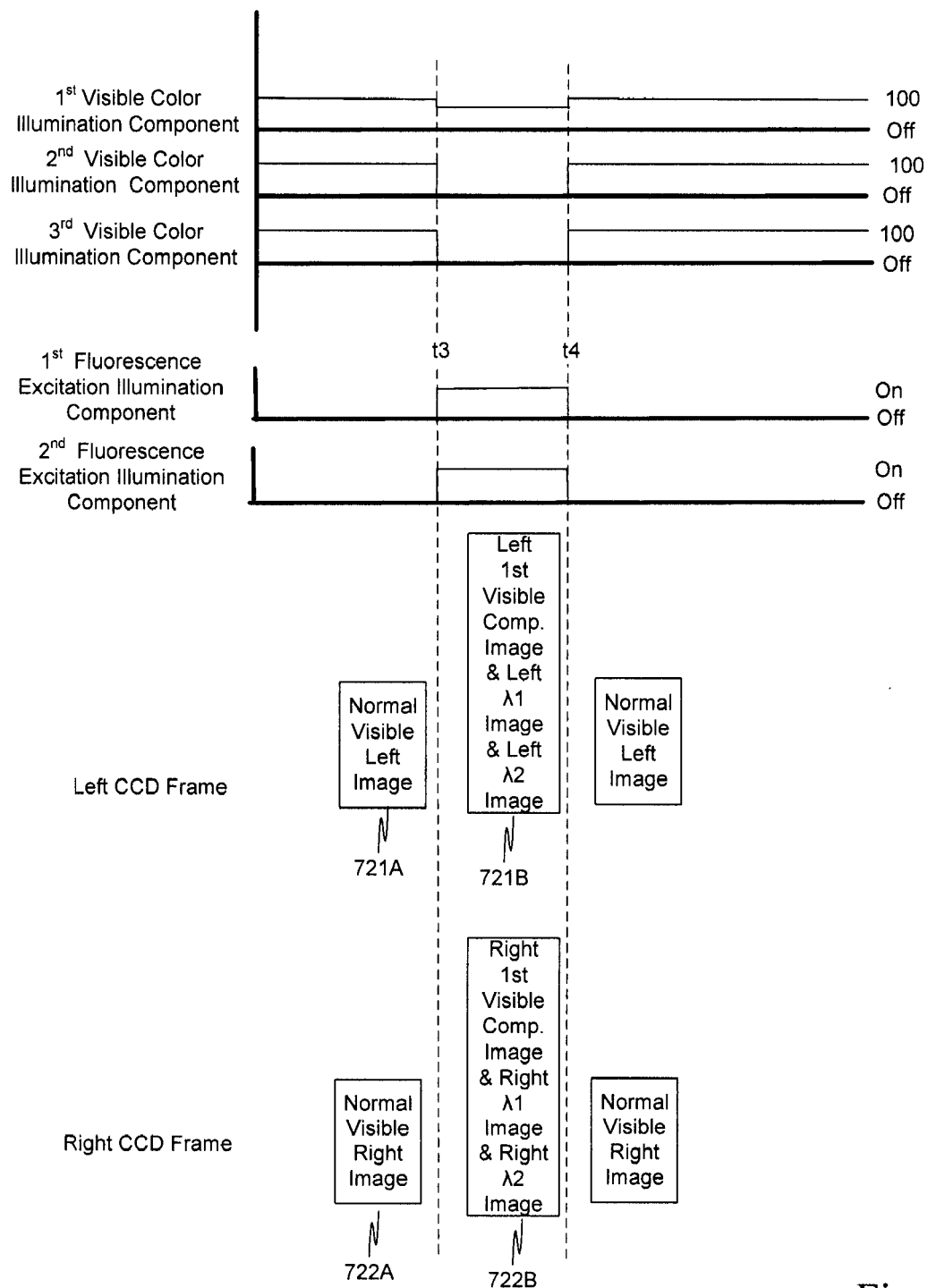
FIG. 7 illustrates another aspect of the timing, synchronization, and capture in the system in FIGS. 2 and 3.

Also, in one embodiment, power and level controller 215 reduces the output level of the first visual color illumination component, e.g., reduces the output level to one part in ten. Thus, as shown in FIG. 7, after time t3, the output level of the first visual color illumination component is reduced relative to the output level prior to time t3, and the second and third visual color illumination component output levels are zero. Also, the first and second fluorescence excitation illumination components are turned on.

The light from tissue 203 (FIG. 2) is passed by the stereoscopic optical path in endoscope 201 to image capture system 220. In one aspect, filters 221B 222B are used to filter any reflected or direct light from the two fluorescence excitation illumination components from fluorescence excitation source 212 before the fluorescence images are captured.

Thus, in CAPTURE IMAGES process 303 (FIG. 3) in the augmented viewing mode, left image CCD 221A captures an acquired left first visible color component image, an acquired left first fluorescence image, and an acquired left second fluorescence image 721B (FIG. 7). Right image CCD 222A captures an acquired right first visible color component image, an acquired right first fluorescence image, and an acquired right second fluorescence image 722B (FIG. 7).

For example, if the third visible color component is the red visible color component and the second visible color component is blue, the green CCD in left image CCD 221A captures the green left visible color component image for the left image. The red CCD in left image CCD 221A captures the left second fluorescence image and the blue CCD in left image CCD 221 captures the left first fluorescence image. Similarly, the green CCD in right image CCD 222A captures the green visible color component images for the right image. The red CCD in right image CCD 222A captures the right second fluorescence image and the blue CCD in right image CCD 222A captures the right first fluorescence image.

In this example, there is neither a second visible color component illumination source nor a third visible color component illumination source. Consequently, light associated with the second and third visible color illumination components is not included in the light from tissue 203. This leaves the CCDs or portions of the CCD, which normally capture the second and third visible color components' light in the images, available to capture the fluorescence images.

Recall, as described above, IMAGE PROCESSING process 304 has received the augmented display signal. Thus, IMAGE PROCESSING process 304 changes from COLOR IMAGE CORRECTION process 231 for images 721B, 722B to AUGMENTED IMAGE CORRECTION process 232.

Figure 8:
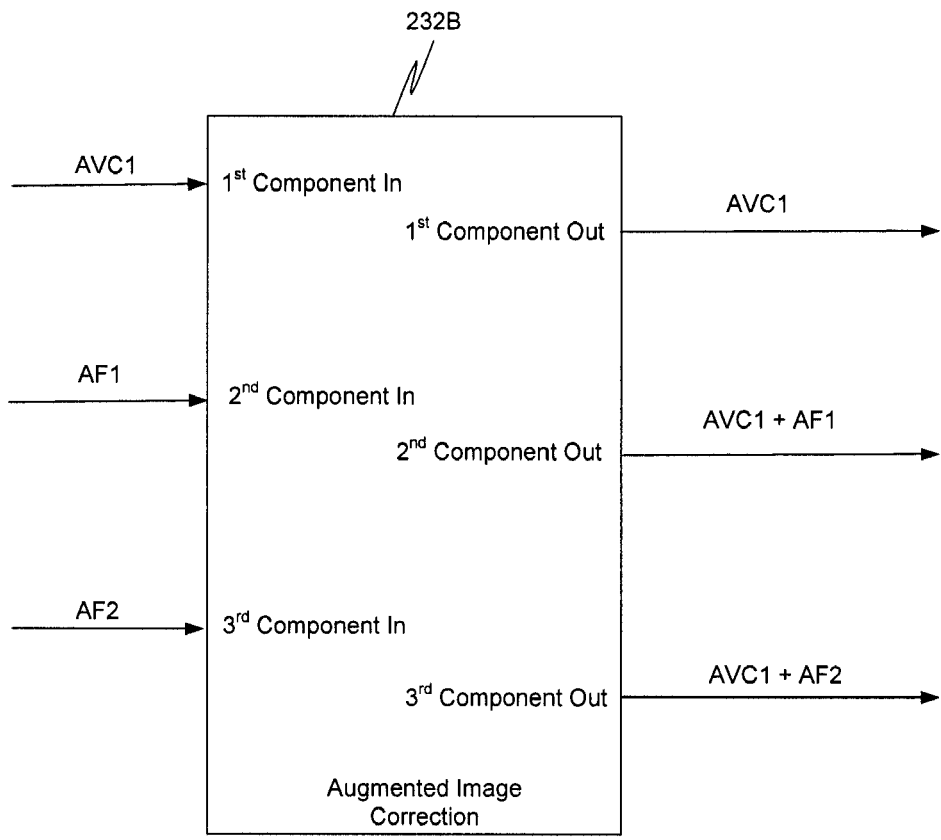
FIG. 8 is a block diagram of another aspect of the augmented image correction process of FIG. 2.

Again, AUGMENTED IMAGE CORRECTION process 232 performs the same process on both the left and right images, and so the left and right designation is not considered in the description. FIG. 8 is a block diagram of the input information to AUGMENTED IMAGE CORRECTION process 232B, and the output information from AUGMENTED IMAGE CORRECTION process 232B.

AUGMENTED IMAGE CORRECTION process 232B receives on a first color component input, acquired first visible color component image AVC1; on second color component input, acquired first fluorescence image AF1; and on a third color component input, acquired second fluorescence image AF2. AUGMENTED IMAGE CORRECTION process 232 again forms the average of the acquired visible color component images for generation of the limited bandwidth visible image, but since only one visible color component image is acquired, the average is acquired first visible color component image AVC1. Each color component of the limited bandwidth image, in this example, is acquired first visible color component image AVC1.

AUGMENTED IMAGE CORRECTION process 232B, in this example, adds acquired first fluorescence image AF1 to the second color component of the limited bandwidth image, which is acquired first visible color component image AVC1, and provides the result to the output for the second visible color component. AUGMENTED IMAGE CORRECTION process 232B also adds acquired second fluorescence image AF2 to the third color component of the limited bandwidth image, which to acquired first visible color component image AVC1, and provides the result to the output for the third visible color component. In this implementation, any pixel which contains both pixel data from image AF1 and pixel data from image AF2 takes on some intermediate color.

In this example, the acquired first visible color component image AVC1 is sent to the first visible color component output. The acquired first visible color component image AVC1 plus the acquired first fluorescence image AF1 is sent to the second visible color component output. The acquired first visible color component image AVC1 plus the acquired second fluorescence image AF2 is sent to the third visible color component output.

The outputs from AUGMENTED IMAGE CORRECTION process 232 are displayed on stereoscopic display 241 (FIG. 2) in GENERATE STEREOSCOPIC VIDEO DISPLAY OF TISSUE process 305 (FIG. 3). In the augmented viewing mode, processes 301 to 305 are performed repetitively so that the surgeon sees a real-time video augmented image of tissue 203.

Thus, during the augmented viewing mode, the surgeon is provided with a three-dimensional limited-bandwidth image of tissue 203 with a first region of interest highlighted in a particular color and a second region of interest highlighted in a different color.

Again, the processing for the augmented display does not introduce any latency and does not require storage of a frame for subsequent processing with a later frame. The processing occurs in real time and so the highlighted portions of the image are always synchronized with the limited-bandwidth monochromatic portion of the image.

When the surgeon wants to change the viewing mode back to the normal stereoscopic color image at time t4 (FIG. 7), the surgeon uses display mode select 250 (FIG. 2) to change the viewing mode to the normal viewing mode. In response to the change, the two fluorescence excitation illumination components in fluorescence excitation source 212 are turned off, the second and third visible color component illumination components are turned on and the first visible color illumination component is returned to the full output level. See FIG. 7. The processing is the same as that described above for the normal viewing mode and so is not repeated.

In the above description, the camera was mounted proximal to the endoscope. However, this is illustrative only and is not intended to be limiting. The process works the same irrespective of the relative locations of the viewing optics and the camera so long as the camera can acquire usable images from the light from the optics. For example, the processes and structures described herein can be utilized with a chip-on-stick endoscope. A chip-on-stick endoscope has a short optics segment with a camera located just behind the optics near the tip of the endoscope.

Also, a stereoscopic endoscope was used as an example. This also is illustrative only and is not intended to be limiting. A monoscopic endoscope could be used in place of the stereoscopic endoscope in the above examples. With the monoscopic endoscope only one of the left and right images would be acquired and processed as described above.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Memory refers to a volatile memory, a non-volatile memory, or any combination of the two. A processor is coupled to a memory containing instructions executed by the processor. This could be accomplished within a computer system, or alternatively via a connection to another computer via modems and analog lines, or digital interfaces and a digital carrier line.

Herein, a computer program product comprises a non-transitory medium configured to store computer readable code needed for any one or any combination of the operations described with respect to the augmented display system or in which computer readable code for any one or any combination of operations described with respect to the augmented display system is stored. Some examples of computer program products are CD-ROM discs, DVD discs, flash memory, ROM cards, floppy discs, magnetic tapes, computer hard drives, servers on a network and signals transmitted over a network representing computer readable program code. A non-transitory tangible computer program product comprises a non-transitory tangible medium configured to store computer readable instructions for any one of, or any combination of operations described with respect to the augmented display system or in which computer readable instructions for any one of, or any combination of operations described with respect to the augmented display system are stored. Non-transitory tangible computer program products are CD-ROM discs, DVD discs, flash memory, ROM cards, floppy discs, magnetic tapes, computer hard drives and other non-transitory physical storage mediums.

In view of this disclosure, instructions used in any one of, or any combination of operations described with respect to the augmented display system can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A surgical system comprising:
   (i) a camera, the camera being configured to capture a first acquired component image and to capture a second acquired component image different from the first acquired component image;
   (ii) a controller connected to the camera, the controller being configured to generate a first visible color component output, the first visible color component output being the first acquired component image, and the first visible color component being a first visible color component of a plurality of color components of white light;
   the controller being configured to generate a second visible color component output, the second visible color component output including the first acquired component image;
   the controller being configured to include the second acquired component image in the second visible color component output so that the second visible color component output is a combination of both the first acquired component image and the second acquired component image, the second visible color component being a second visible color component of the plurality of color components of white light, and the second acquired component image comprising a fluorescence image excited by a fluorescence excitation illumination component; and
   the controller being configured to generate a third visible color component output, the third visible color component output being the first acquired component image, the third visible color component being a third visible color component of the plurality of color components of white light;
   (iii) a display connected to the controller, the display connected to the controller being configured to receive the first visible color component output on a first visible component input of the display, the second visible color component output on a second visible component input of the display, and the third visible color component output on a third visible component input of the display, the display being configured to display the first, second and third visible color component outputs to obtain a monochromatic image combined with the second acquired component image, and the second acquired component image being highlighted relative to the monochromatic image, the monochromatic image combined with the second acquired component image being a combination of the first, second, and third visible color component outputs.

2. The system of claim 1, further comprising:
   an illuminator, the illuminator being configured to provide simultaneously at least two illumination components, wherein one of the illumination components comprises the fluorescence excitation illumination component, and wherein other illumination components include less than all the plurality of visible color illumination components of white light illumination.

3. The system of claim 2,
   the other illumination components including a first visible color illumination component;
   and the first acquired component image comprising an acquired first visible color component image.

4. The system of claim 2, the other illumination components including a first visible color illumination component and a second visible color illumination component.

5. The system of claim 4, the camera further being configured to capture a third acquired component image, the first acquired component image being an acquired first visible color component image; the second acquired component image being an acquired fluorescence image; and the third acquired component image being an acquired second visible color component image.

6. The system of claim 5, the controller being configured to generate the first and third visible color component outputs from the acquired first and second visible color component images; and the controller being configured to generate the second visible color component output from the acquired first and second visible color component images and the acquired fluorescence image.

7. The system of claim 6, the first visible color component output being a blue color component output, and the second visible color component output being a green color component output.

8. The system of claim 6, the second visible color component output being a green color component output.

9. The system of claim 2, the other illumination components comprising a first visible illumination component and a second fluorescence excitation illumination component.

10. The system of claim 9, the camera further being configured to capture a third acquired component image, the first acquired component being an acquired first visible color component image; the second acquired component image being an acquired first fluorescence image; and the third acquired component image being an acquired second fluorescence image.

11. The system of claim 10, the controller being configured to add the third acquired component image to the third visible color component output.

12. The system of claim 2, the illuminator including:
a first visible color illumination component source;
a second visible color illumination component source, the second visible color illumination component being different from the first visible color illumination component;
a third visible color illumination component source, the third visible color illumination component being different from the second visible color illumination component, and different from the first visible color illumination component; and
a fluorescence excitation illumination source; and
the system further comprising:
a power level and power supply controller connected to the first, second, and third visible color component illumination sources, and to the fluorescence excitation illumination source; and
a mode changer coupled to the power level and power supply controller, the mode changer having a first state and a second state,
when the mode changer has the first state, the power level and power supply controller (a) being configured to provide power to the first, second, and third visible color illumination component sources, and not to the fluorescence excitation illumination source, and (b) the first, second, and third visible color illumination component sources each having a first level of illumination; and
when the mode changer has the second state, the power level and power supply controller (a) being configured to provide power to the first visible color illumination component source, to at least a portion of the second visible color illumination component source and to the fluorescence excitation illumination source, and not to the third visible color illumination component source, and (b) being configured to reduce the levels of illumination of the first visible color illumination component source and the second visible color illumination component source.

* * * * *